United States Patent
Gederi et al.

(10) Patent No.: US 12,154,270 B2
(45) Date of Patent: Nov. 26, 2024

(54) METHOD AND SYSTEM FOR THE ANALYSIS OF MEDICAL IMAGES

(71) Applicant: Optellum Limited, Oxford (GB)

(72) Inventors: Elnaz Gederi, Oxford (GB); Carlos Federico Areta Montilva, Oxford (GB)

(73) Assignee: Optellum Limited, Oxford (GB)

(*) Notice: Subject to any disclaimer, the term of this patent is extended or adjusted under 35 U.S.C. 154(b) by 478 days.

(21) Appl. No.: 17/507,671

(22) Filed: Oct. 21, 2021

(65) Prior Publication Data
US 2023/0125090 A1     Apr. 27, 2023

(51) Int. Cl.
| | |
|---|---|
| *G06T 7/00* | (2017.01) |
| *A61B 6/00* | (2006.01) |
| *A61B 8/08* | (2006.01) |
| *G06F 18/214* | (2023.01) |
| *G06F 30/10* | (2020.01) |
| *G16H 10/60* | (2018.01) |
| *G16H 30/20* | (2018.01) |

(Continued)

(52) U.S. Cl.
CPC .......... *G06T 7/0012* (2013.01); *A61B 6/5217* (2013.01); *A61B 8/5223* (2013.01); *G06F 18/214* (2023.01); *G06F 30/10* (2020.01); *G16H 10/60* (2018.01); *G16H 30/20* (2018.01); *G16H 30/40* (2018.01); *G16H 50/20* (2018.01); *G16H 50/30* (2018.01); *G06T 2207/20081* (2013.01); *G06T 2207/20084* (2013.01); *G06T 2207/30061* (2013.01)

(58) Field of Classification Search
CPC ......... G06T 7/0012; G06T 2207/20081; G06T 2207/20084; G06T 2207/30061; G06T 2207/10072; A61B 6/5217; A61B 8/5223; G06F 18/214; G06F 30/10; G16H 10/60; G16H 30/20; G16H 30/40; G16H 50/20; G16H 50/30; G16H 50/70; G16H 50/70382

See application file for complete search history.

(56) References Cited

U.S. PATENT DOCUMENTS

2021/0287795 A1*   9/2021   Declerck ............... G16H 30/20
2021/0312629 A1*   10/2021   Cheng ..................... G06T 7/11

(Continued)

OTHER PUBLICATIONS

Guang Li et al, A novel four-dimensional radiotherapy planning strategy from a tumor-tracking beam's eye view, Article in Physics in Medicine and Biology—Oct. 2012, pp. 7579-7598.

(Continued)

*Primary Examiner* — Md K Talukder
(74) *Attorney, Agent, or Firm* — Optimus Patents US, LLC

(57) ABSTRACT

A CADx system for analysing medical images for determining if the images are acceptable for analysis, by identifying the respiratory state of the lungs as shown in an image is described. The system comprising: an input circuit for receiving at least one image; a respiratory state assessor circuit for determining the respiratory state of the lungs in the input image where the respiratory state assessor is trained with a plurality of training images showing a range of different respiratory states, and an output circuit to produce an output confirming the respiratory state of the input image. A method of analysing images, and a method of training a machine learning model to recognize different respiratory states are also described.

16 Claims, 5 Drawing Sheets

(51) Int. Cl.
*G16H 30/40* (2018.01)
*G16H 50/20* (2018.01)
*G16H 50/30* (2018.01)

(56) References Cited

U.S. PATENT DOCUMENTS

| | | | |
|---|---|---|---|
| 2022/0022818 A1* | 1/2022 | Ghesu | G06T 7/0012 |
| 2023/0125090 A1* | 4/2023 | Gederi | G16H 50/30 |
| | | | 382/128 |

OTHER PUBLICATIONS

Michele Gaeta et al, Expiratory CT scan in patients with normal inspiratory CT scan: a finding of obliterative bronchiolitis and other causes of bronchiolar obstruction, . Multidisciplinary Respiratory Medicine 2013, pp. 1-8.

Alexander A. Bankier et al, Recommendations for Measuring Pulmonary Nodules at CT: A Statement from the Fleischner Society, Radiology: vol. 285, pp. 584-600.

David R Baldwin et al, The British Thoracic Society guidelines on the investigation and management of pulmonary nodules, Thorax 2015;70:794-798.

EPO Serial No. 22200576.1-1126; EPO Article 94(3) Communication, Feb. 23, 2024; pp. 1-8.

* cited by examiner

METHOD AND SYSTEM FOR THE ANALYSIS OF MEDICAL IMAGES

FIELD OF INVENTION

This invention relates to the field of Computer Aided Diagnosis (CADx) systems and methods for assisting the interpretation of medical images to support clinicians in healthcare. In particular, the field relates to risk Computer Aided Diagnosis systems that can determine the respiratory state of lung tissue shown in the images.

BACKGROUND OF INVENTION

In the field of medical imaging, a variety of technologies can be used to investigate biological processes and anatomy. The following examples are types of scans that may be used to provide medical images: X-Ray; Computed Tomography (CT); Ultrasound (US); Magnetic Resonance Imaging (MRI); Single Photon Emission Tomography (SPECT); and Positron Emission Tomography (PET). Each type of scan is referred to as an "imaging modality".

Typically, a scan provides a "dataset". The dataset comprises digital information about the value of a variable at each of a plurality of spatial locations in either a two-dimensional or (more typically) a three-dimensional space. As a specific example, a CT scan may provide images of the chest of a patient. Such a CT scan might, as a more specific example, show lung nodules in the chest.

Computer Aided Detection (CADe) devices serve to assist its users (e.g. typically clinicians) in assessing the medical images. CADe devices need to provide a clinician with standardised, objective and repeatable information. The information typically relates to particular anatomical regions, including both normal tissue and lesions, within a person. CADe devices may be used as a so-called 'Second Reader' system. Second Reader Systems are based on an approach whereby a radiologist first looks at an image resulting from a scan, for example a mammogram. The radiologist will then, based on training and experience, identify areas of the scan where the radiologist considers that there may need to be a further investigation, for example a biopsy. However, the radiologist can then consider the CADe findings. Those findings might involve a display to highlight any additional suspicious regions on the mammogram. The radiologist will then, based on training and experience, look at those further areas of the scan. The CADe device is thereby performing a second look at the scan. The results of the second look at the scan may be that the radiologist will be directed to areas of the scan that he/she had overlooked. In this way, CADe devices are designed to reduce 'false negatives', which are also termed 'missed findings'. Thus, CADe devices perform a support role to clinicians.

Computer Aided Diagnosis (CADx) devices are a related technology to CADe. CADx devices attempt to solve a different problem and relate generally to risk assessment. Instead of focussing on potentially missed findings as in CADe, they try to assist the user to classify findings correctly, either as malignant or benign in the case of potentially cancerous lesions. They rely on the user to identify abnormalities, but then typically provide a score that is indicative of the risk of malignancy. There are many examples of such CADx devices proposed within the academic literature. However, few systems are available commercially, and hence used in clinical practice. This discrepancy is indicative of the difficulties in deploying practical systems with the known approaches. The output of known CADx devices is typically some kind of score. That score indicates the risk or likelihood of disease, or its absence. An example of a commercial CADx device is the 'Transpara™' product from 'Screenpoint™'. There are many non-clinical CADx devices in the academic literature.

State-of-the-art CADx devices are built around machine learning models. These models are generic algorithms with "learnable" parameters which are fitted using training data such that the model can be used to make predictions on previously unseen data. For example, a machine learning model built to predict whether a lung nodule on a CT image is malignant, can be fitted to a collection of datasets of CT images of malignant and benign lung nodules. Such a model could then be suited to assist a clinician in estimating the risk that a lung nodule they found in their practice could be malignant. The process of fitting the model parameters to the training data is referred to as the model training, while the process of using the model to make a prediction on input data is referred to as inference. The output of the inference in the case of a machine learning-based CADx device would typically be a score indicative of the likelihood that the input sample contains the disease of interest, for instance a score for malignancy in the case of the lung nodules.

When using medical images in the diagnosis of a lung disease, it is often the case that a specific respiratory state of the patient is recommended during the acquisition of the image. This aims to reduce unnecessary image variability in the form of changes in the appearance of relevant anatomical structures that are due to the expansion and contraction of the lungs for different respiratory states. FIG. 1 illustrates an example of the image variability due to changes in the respiratory state [1]. As FIG. 1 shows, some example respiratory related changes to the lung are changes to the volume and therefore the intensity of the parenchyma in medical images (in full-exhalation parenchyma appears with a higher intensity) and changes to the morphology of the nodules. In the case of diagnosing lung cancer from CT images, it is generally recommended for the CT image to be acquired at full inhalation [2, 3]. Otherwise, critical measurements such as the size of a lung nodule will depend on the respiratory state and may no longer be directly comparable to recommendations in clinical guidelines. Likewise, using a machine learning model to make predictions on medical images that are not acquired at the optimal respiratory state (e.g., the respiratory state in which the training data was acquired) is considered a misuse of the model as its performance cannot be assured. That is, before being used for inference in a real setting, the model is characterised. During characterisation, the frequency at which a model makes different kinds of errors when performing its task is measured and recorded in a report, for instance the frequency with which the model incorrectly classifies malignant lung nodules as benign and vice-versa may be measured. When medical images that are not acquired at the right respiratory state are encountered at inference time, the model might make errors more frequently than the model characterisation will have reported, and this will not be apparent to the user, i.e., the user will make clinical decisions using a model that makes errors more often than they have been led to expect. An example of this scenario is a machine learning model for lung cancer prediction that is trained using CT images with patient at full-inhalation but is used on CT data that was not acquired at full-inhalation. In such a case, the performance of the model at inference time could be worse than when the model was tested by the manufacturers.

Medical images in respiratory states other than the expected respiratory state could be input into the CADx device either by mistake, lack of awareness, or an unwillingness to strictly enforce the expected respiratory state. For example, a patient may be indicated to hold their breath at full inhalation, and still the resulting image could be at partial inhalation because of the inability of the patient to hold their breath at full inhalation due to an underlying lung condition. Alternatively, a medical image might have been acquired for a different purpose, for example, the assessment of air-trapping in lung conditions such as emphysema or small-airway disorder [4] where full inhalation may not be part of the protocol, and still reveal a lung nodule requiring cancer diagnosis. The user, ambivalent to the expected respiratory state, might attempt to obtain a risk assessment from the CADx device.

Using medical images at unexpected respiratory states in a CADx device can be of particular concern when multiple images of the same patient, taken at different points in time, are simultaneously assessed for temporal changes in the condition of interest; for example, comparing an image from when a condition was first detected, with an image collected at a follow-up examination. An example of a diagnostic process typically requiring temporal assessment is lung cancer, where the progression of lung nodules as seen in CT images can be a determinant factor for clinical decision making. This is because lung nodules which appear to reduce in size without any cancer treatment are generally considered to be benign lesions. Likewise, when nodules appear to grow, they become highly suspicious of being cancerous, and candidates for invasive procedures such as biopsy. It is possible for an apparent change in size of a lung nodule to be caused by a difference in the respiratory state of the patients in each of the images being compared, which could lead to either an unnecessary invasive procedure being done on a benign lesion, or a cancerous lesion being diagnosed later than would have been possible. Therefore, it is critical to prevent such misleading images from being assessed by a CADx device which, unlike medical experts, could be ignorant of external causes to the apparent progression of the condition of interest.

In summary, CT images that are not acquired at the expected respiratory state are a major risk when state-of-the-art CADx devices are used in clinic, even in seemingly highly controlled scenarios such as lung cancer prediction from CT images. Therefore, there is a need for detecting unexpected respiratory states and make the clinician aware of the risks associated with using the CADx device under such condition.

REFERENCES

[1] Li G, Cohen P, Xie H, Low D, Li D, Rimner A. A novel four-dimensional radiotherapy planning strategy from a tumor-tracking beam's eye view. Phys Med Biol. 2012 Nov. 21; 57(22):7579-98. doi: 10.1088/0031-9155/57/22/7579. Epub 2012 Oct. 26. PMID: 23103415.

[2] Callister M E, Baldwin D R, Akram A R, Barnard S, Cane P, Draffan J, Franks K, Gleeson F, Graham R, Malhotra P, Prokop M, Rodger K, Subesinghe M, Waller D, Woolhouse I; British Thoracic Society Pulmonary Nodule Guideline Development Group; British Thoracic Society Standards of Care Committee. British Thoracic Society guidelines for the investigation and management of pulmonary nodules. Thorax. 2015 August; 70 Suppl 2:ii1-ii54. doi: 10.1136/thoraxjnl-2015-207168. Erratum in: Thorax. 2015 December; 70(12):1188. PMID: 26082159.

[3] Bankier A A, MacMahon H, Goo J M, Rubin G D, Schaefer-Prokop C M, Naidich D P. Recommendations for Measuring Pulmonary Nodules at CT: A Statement from the Fleischner Society. Radiology. 2017 November; 285(2):584-600. doi: 10.1148/radiol.2017162894. Epub 2017 Jun. 26. PMID: 28650738.

[4] Gaeta M, Minutoli F, Girbino G, Murabito A, Benedetto C, Contiguglia R, Ruggeri P, Privitera S. Expiratory CT scan in patients with normal inspiratory CT scan: a finding of obliterative bronchiolitis and other causes of bronchiolar obstruction. Multidiscip Respir Med. 2013 Jul. 9; 8(1):44. doi: 10.1186/2049-6958-8-44. PMID: 23835554; PMCID: PMC3710098.

SUMMARY OF THE INVENTION

Accordingly, the invention seeks to mitigate, alleviate, or eliminate one or more of the above mentioned disadvantages singly or in any combination.

According to the invention there is provided a CADx system for reviewing medical images to determine if the images are acceptable for further analysis by the CADx system, by identifying the respiratory state of the lungs as shown in a medical image, the system comprising: an input circuit for receiving at least one medical image; a respiratory state assessor circuit for determining the respiratory state of the lungs in the input medical image where the respiratory state assessor is trained with a plurality of training images showing a range of different respiratory states, and an output circuit to produce an output confirming the respiratory state of the input image.

In a preferred embodiment of the invention the output is a warning about the respiratory state of the input image that the input image is not an acceptable state. Further preferably, the warning is one or more of an audio or visual warning.

In an embodiment of the invention the CADx system will further analyse the input image when, after review of the input image has a warning about the acceptability of the input image.

Further preferably, when the output circuit confirms that the respiratory state of input image is an acceptable respiratory state, the image is passed for further analysis by the CADx system.

Preferably, the output from the further analysis comprises a disease risk score for the input image.

In an embodiment of the invention, the input image is one of: a CT image, an MRI image, a PET image, an X-ray image, an ultrasound image, or a SPECT image. Preferably, the input image comprises an image showing at least part of a lung Preferably, the input further comprises one or more of: biomarkers for the patient or clinical parameters for the patient. Further preferably, the clinical parameters and biomarkers comprise at least one of: patient age, patient sex, results of blood tests, results of lung function tests.

In an embodiment of the invention, the respiratory state assessor circuit determines the respiratory state of the input image by generating a respiratory state signal y and comparing the signal to a predefined threshold, where the input image is acceptable if the respiratory state signal exceeds the threshold.

Preferably, the output of the CADx system is determined according to the following threshold relationship:

$$\text{CADx Output} = \begin{cases} \textit{DiseaseRiskscore}, & y \geq TH_{Resp} \\ \textit{DiseaseRiskscore and RespiratoryStateWarning}, & y < TH_{Resp} \end{cases}$$

where $TH_{resp}$ is the respiratory threshold.

In an embodiment of the invention, the threshold can determine if the input image shows full exhalation, partial inhalation, or full inhalation. Preferably, the exhalation status is determined by:

$$\textit{PercentageInhalation} = \begin{cases} \text{Full exhalation}, & y < TH_{lvl1} \\ \text{Partial inhalation}, & TH_{lvl1} \leq y < TH_{lvl2} \\ \text{Full inhalation}, & y \geq TH_{lvl2} \end{cases}$$

where $TH_{lvl1}$ and $TH_{lvl2}$ are inhalation thresholds.

In a further embodiment of the invention there is provided a method for analysing medical thoracic images for determining if the images are acceptable for analysis, by identifying the respiratory state of the lungs as shown in a medical image, the method comprising the following: receiving at least one input medical image; determining the respiratory state of the lungs in the input medical image using a respiratory state assessor, where the respiratory state assessor is trained with a plurality of training images showing a range of different respiratory states, and producing an output confirming the respiratory state of the input image.

Preferably, the output is a visual or audio warning about the respiratory state of the input image.

In a preferred embodiment of the invention, the method further comprising the step of providing the input image to a CADx system for further analysis of the input image when the input image has a warning about the acceptability of the input image.

In an embodiment of the invention there is provided a method of training a Machine Learning model to recognise different respiratory states comprising the steps of providing a training dataset of input images with corresponding ground truth labels: providing at least one image from the training set to a respiratory state predictor to output a respiratory state prediction; comparing the respiratory state prediction with the corresponding ground truth label to determine the accuracy of the ML model; repeating the above steps until the variation between the prediction and the ground truth level reaches a pre-set level.

Preferably, the method further comprising the step of using a loss function to compare the respiratory state prediction with the corresponding ground truth label.

In an embodiment of the invention the ML model further comprises an optimisation algorithm to optimise the loss function.

Preferably, the respiratory state predictor comprises a neural network.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION

Overview of the Invention

In the context of a CADx device that is based on a machine learning model to produce a lung disease risk score for input medical data, a preferred embodiment of this invention addresses the need for alerting the user if the input image was not acquired at the expected respiratory state. In an example of the invention, this is achieved through the assessment of the respiratory state from the medical scan image. Preferably the assessment of the respiratory state is automatic. Therefore, central to this invention is the respiratory state assessor (RSA), a circuit which forms part of the CADx device and reviews the input data to identify scan images that are not acquired at the expected respiratory state. Preferably the input scan image is a CT scan, but other imaging modalities may include an MRI image, a PET image, an X-ray image, an ultrasound image, or a SPECT image. In a preferred embodiment of the invention, the scan is a thoracic image, but any scan image which shows at least part of the lungs will be suitable. When the RSA identifies input data that is not acquired at the expected respiratory state, the user is warned that the respiratory state of the input data is not optimal for a reliable risk score from the input image. Preferably the input data will still be analysed by the CADx system to generate a risk score for the input image, but the user will be aware that the respiratory state shown in the image is not ideal. For CADx devices which accept medical images from multiple timepoints such that they can consider temporal changes between the images, an extension of the RSA further assesses whether the respiratory state between the multiple timepoints is similar, and if not, the user is warned that the multi-timepoint sequence of medical images is not suitable for obtaining a risk score for the disease of interest.

Figure 2:
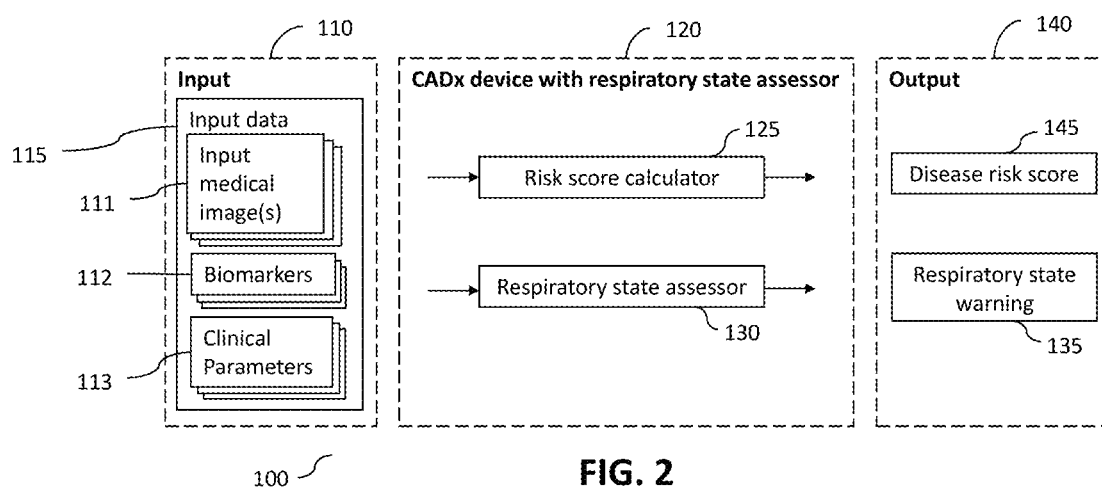
FIG. 2 illustrates a CADx system according to an embodiment of the invention.

In more detail, FIG. 2 illustrates an embodiment of the invention showing a CADx device (120) with the respiratory State Assessor, RSA (130). This figure shows a CADx system (100) with input (110), machine learning based CADx device (120) with an RSA circuit (130) and output (140). In this example of the invention, the input (110) to the CADx device (120) is a unit of input data (115) containing at least one medical image (111) in which at least part of the lungs of the patient are visible. In an embodiment of the invention, the input (110) further comprises one or more of: biomarkers (112) for the patient or clinical parameters (113) for the patient. Preferably, the biomarkers and clinical parameters comprise at least one of: patient age, patient sex, results of blood tests, results of lung function tests.

Like standard CADx devices, when the input data (115) is presented to the input circuit (110) of the CADx device (120), the data is processed by a risk score calculator (125). In a preferred embodiment of the invention the risk score calculator is based on a machine learning model that is trained to predict a risk score of a disease given the input data (115). Specifically, the risk score calculator (125) performs a series of mathematical operations on the values of the input data (115) resulting in a disease risk score (145) that is provided via the output circuit (140). Unlike standard CADx devices, the CADx device (120) with RSA (130) includes a circuit capable of reviewing the input image to assess the patient's respiratory state at the moment the input image was acquired, and then determining whether the respiratory state of the input image (111) matches the expected respiratory state for the CADx device (120). The output circuit will produce an output confirming the respiratory state of the input image. In a preferred embodiment of the invention the RSA (130) is typically based on a machine learning model, processing the input data (115) through mathematical operations, which eventually result in a binary decision of whether the user should be prompted with a warning (135) that the input data was not acquired at the expected respiratory state.

In an embodiment of the invention, if no warning about the respiratory state is provided after the image has been reviewed, and the respiratory state of the lungs in the input image is an acceptable respiratory state for the input image, then the CADx system will further analyse the input scan image (111) in the usual manner. If a warning about the respiratory state is provided after the image has been reviewed, then the user will be aware that the respiratory state is not the usual acceptable state, and can bear this in mind when reviewing the results of the further CADx analysis showing the disease risk score for example. In some embodiments of the invention, the user may decide not to proceed with the further analysis of the scan image to obtain a disease risk score if a warning about the suitability of the respiratory state is received.

Implementation of the CADx Device with Respiratory State Assessor

Figure 3:
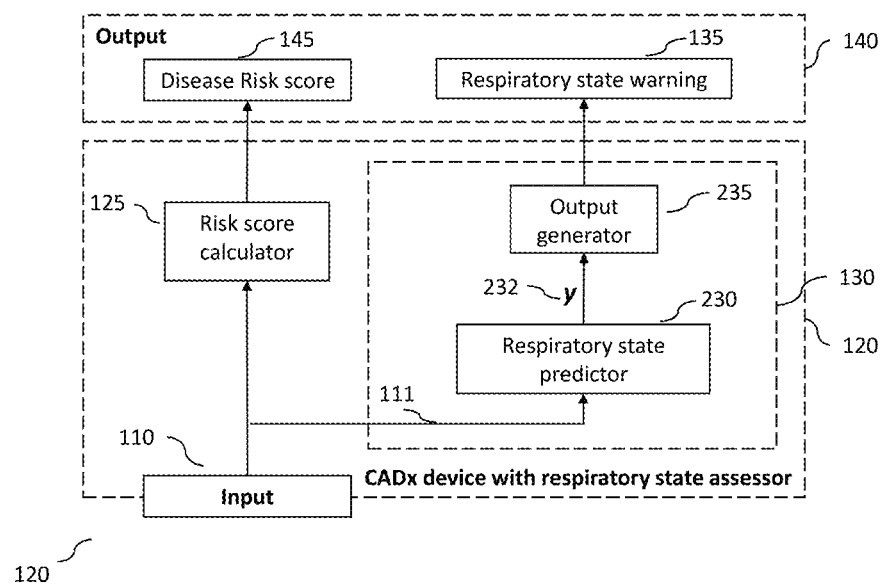
FIG. 3 show a high-level implementation of the CADx system with a respiratory state assessment circuit according to an embodiment of the invention.

FIG. 3 shows the diagram of an example implementation of a CADx device (120) with an RSA (130). Central to the CADx device (120) is a machine learning model for disease prediction (125) that receives input data through the input circuit (110) and may provide a disease risk score (145) for the input image. Preferably the disease is a lung disease, such as lung cancer, but other diseases are possible.

Parallel to the risk score calculator (125) is the respiratory state assessor RSA (130). In some examples of this invention, the RSA (130) consists of a respiratory state predictor circuit (230) which reviews the input image, and can output a respiratory state prediction signal y (232) that is indicative of the respiratory state of the patient at the moment the input image was acquired.

In some examples of this invention, the respiratory state predictor (230) is based on a machine learning model with model parameters θ derived such that the model is able to estimate the respiratory state of the patient as captured on a medical image. The derivation of the model parameters θ is through an iterative series of mathematical operations and is referred to as the model training process.

Figure 1:
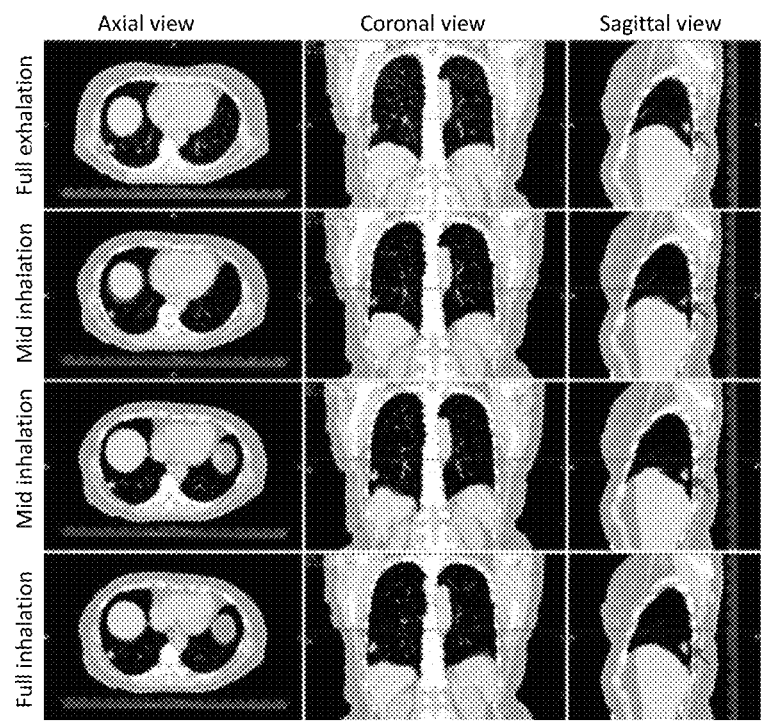
FIG. 1 illustrates an example of the image variability due to changes in the respiratory state.
Figure 4:
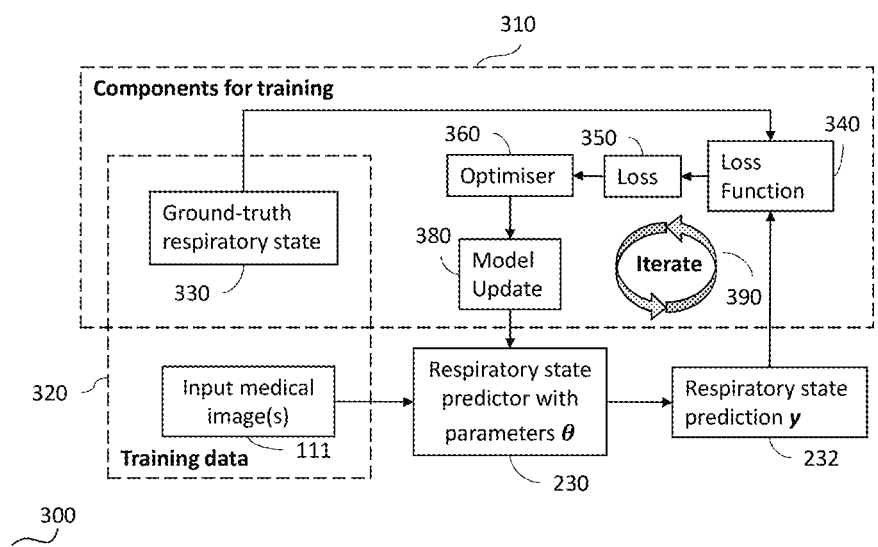
FIG. 4 shows an example of the fitting process of a distribution model for the training data.

An example training process is shown in FIG. 4. This training process relies on a training dataset (320), a collection of pairs of medical images (111) and corresponding ground-truth labels (330), which indicate the respiratory state at which the image was acquired, for example, full exhalation, mid-inhalation, or full inhalation, as shown in the examples in FIG. 1. Preferably the training images will show a range of different respiratory states. There is no restriction in the age or sex of the patients with images in the training dataset. In an embodiment of the invention, the training process may entail inputting at least one medical image from the training dataset (320) to the respiratory state predictor (230), which outputs the respiratory state prediction y (232). This prediction (232) is then compared to the corresponding ground-truth respiratory state (330) preferably by using a loss function (340) which is chosen to measure how accurately the model predicts the ground-truth respiratory state given the associated data. In some examples of the invention, an optimiser (e.g., 360) running an optimisation algorithm may be used to reduce the loss (350), the output of the loss function (340), i.e. to improve the model's performance, by measuring how much each model parameter θ contributed to the loss, and using the information to update the model parameters θ (380) in such a way as to reduce the loss (350). Each of such updates is referred to as an iteration (390). The model training iterations are terminated when the model has reached convergence, that is when the variation between the prediction and the ground truth level reaches a pre-set level, which is when the validation data loss does not decrease compared to the previous iterations. Once the iterations are stopped, the respiratory state predictor (230) can be used to estimate the respiratory state on input medical data without requiring any of the training components (310). In some examples of the training process, the training dataset (320) may contain medical images of patients at full inhalation, full exhalation, or partial inhalation, or any combination of images in these three different states. In some examples of this case, the loss function (340) is a cross entropy function, commonly used to train modern machine learning models. In other examples of the invention, other loss functions such as L2, Hinge, and Kullback Leibler Divergence may be used.

Figure 5:
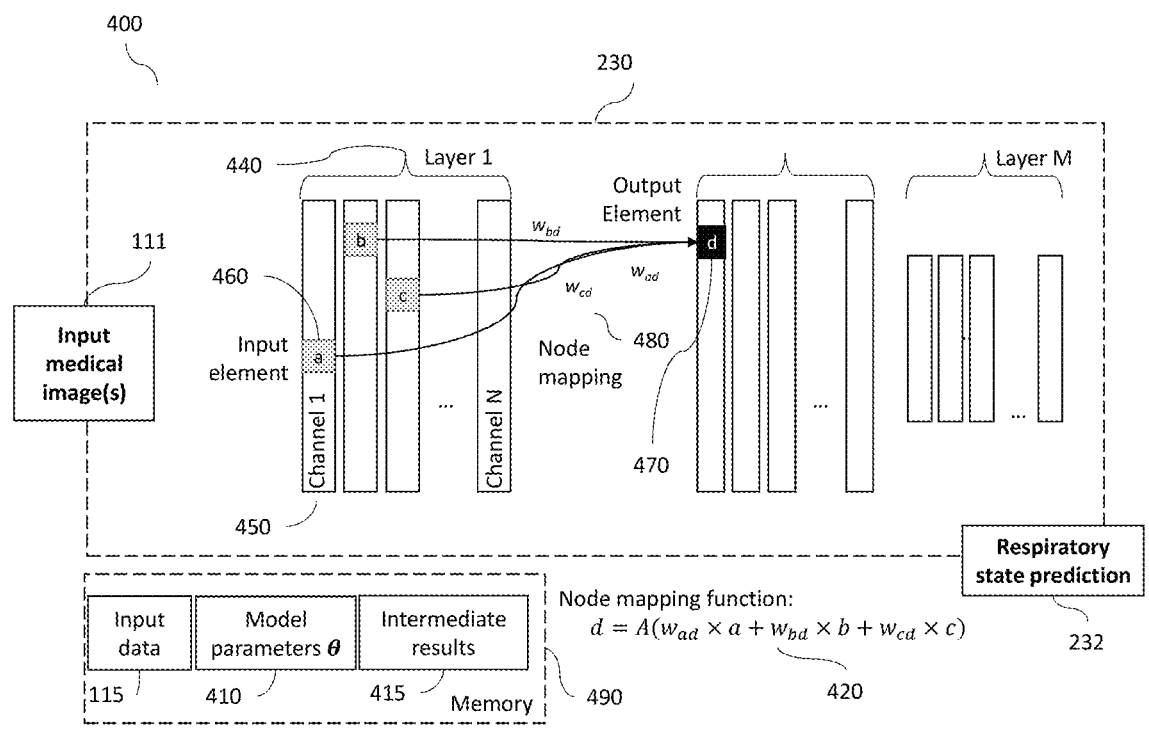
FIG. 5 shows an example of a neural network as used in an embodiment of the invention.

In some examples of the invention, the respiratory state predictor comprises of a neural network (DNN) (400) (FIG. 5), which applies a series of node mappings (480) to an input medical image (111), which ultimately resolves into a scalar output corresponding to the respiratory state prediction (232). Preferably the neural network is a deep neural network. The example DNN (400) comprises a consecutive sequence of network layers (e.g. layers (440)), each of which consists of a series of channels (450). The channels are further divided into input elements (460). In this example, each input element (460) stores a single value. Some (or all) input elements (460) in an earlier layer are connected to the elements in a later layer by node mappings (480), each with an associated weight. For each node mapping (480), the elements in the earlier layer are referred to as input elements (460) and the elements in the output layer are referred to as the output elements (470). An element may be an input element to more than one node mapping, but an element is only ever the output of one node mapping function (420).

In order to calculate the output (232) of the DNN (400) the system first considers the input medical image as the earlier layer. The layer(s) to which the earlier layer is connected by a node mapping function (420) are considered in turn as the later layer. The value for each element in later layers is calculated using the node mapping function (420) in equation 1.5, where the values in the input elements (460) are multiplied by their associated weight in the node mapping function (420) and summed together.

Node mapping function (420):

$$d = A(w_{ad} \times a + w_{bd} \times b + w_{cd} \times c) \tag{1.5}$$

The result of the summing operation is transformed by an activation function, 'A' and stored in the output element (470). The DNN (400) now treats the previously considered later layer(s) as the earlier layer, and the layers to which they are connected as the later layers. In this manner DNN (400) proceeds from the input layer (440) until the value(s) in the output prediction signal, y (232), have been computed.

In some examples of the invention, the large number of parameters used in the neural network may require the device to include a memory (490). Preferably, the memory (490) may be used to store the input data (115), the model parameters (410), and the intermediate results of the node mappings (415).

In other examples of the invention, other machine learning algorithms such as support vector machines or decision trees can be used as the basis for the RSA.

Once the respiratory state signal y (232) is calculated it is then input into an output generator (235), whose function is to decide, based on the respiratory state signal y (232), whether to issue a respiratory state warning (135) to the output circuit (140) of the CADx device that the respiratory state of the input image is not an acceptable state. In a preferred embodiment of the invention the warning is presented as a visual or audio message to the user, but the warning may be presented in other alternative ways as well. In some examples of the invention, the decision to issue a respiratory state warning is done based on a predefined threshold $TH_{Resp}$, below which the respiratory state of the input data is considered unacceptable for obtaining a reliable disease risk score from the CADx device, and above which the input image is acceptable. That is, $$CADx \text{ Output} = \begin{cases} DiseaseRiskscore, & y \geq TH_{Resp} \\ DiseaseRiskscore \text{ and } RespiratoryStateWarning, & y < TH_{Resp} \end{cases} \quad (1.1)$$

Generally, setting $TH_{Resp}$ is a process of assessing the trade-offs between a high $TH_{Resp}$, which may lead to issuing warnings too frequently and negatively affect the usability of the CADx device, and a low $TH_{Resp}$, which may miss many datasets with unacceptable respiratory states and does not fulfil the respiratory state assessment purpose. Therefore, $TH_{Resp}$ must be set through a careful process of risk assessment of the specific use case of the CADx device.

In another example of the invention, when issuing a respiration state warning, the CADx device also outputs a label indicative of the percentage of inhalation computed based on the respiratory state signal y (232), which provides the user with more information to decide to how to use the disease risk score in their decision making given the respiratory state warning. For example, respiratory state signal y (232) is translated into labels of full exhalation, partial inhalation, and full inhalation for an input image in the following way:

$$PercentageInhalation = \begin{cases} \text{Full exhalation,} & y < TH_{Ivl1} \\ \text{Partial inhalation,} & TH_{Ivl1} \leq y < TH_{Ivl2} \\ \text{Full inhalation,} & y \geq TH_{Ivl2} \end{cases} \quad (1.2)$$

where $TH_{Ivl1}$ and $TH_{Ivl2}$ are inhalation thresholds that may be defined based on the inspection of the value of the respiratory state signal y (232) on a set of example medical images containing cases of images acquired at full exhalation, partial inhalation, and full inhalation. Setting $TH_{Ivl1}$ is a process of assessing the trade-offs between a high $TH_{Ivl1}$, which may lead to wrongly categorising too many medical images as full exhalation, and a low $TH_{Ivl1}$, which may miss many medical images acquired in full exhalation. Similarly, setting $TH_{Ivl2}$ is a process of assessing the trade-offs between a high $TH_{Ivl2}$, which may lead to missing many medical images acquired in full inhalation, and a low $TH_{Ivl2}$, which may lead to wrongly categorising too many medical images in full inhalation. The provision of the inhalation/exhalation label can be used, along with the disease risk score so that the user can ignore a warning about the respiratory state, if the user considers that the state as shown is acceptable.

In another example of the invention, where the CADx device (120) is designed to accept sequences of medical images of the same patient collected at different points in time in order to assess progression of a lung condition. The interval between time points may vary depending on patient information and lung condition. In some cases, a second medical scan is performed within minutes of the first scan. In other cases, a follow-up scan may be done a few months or years later. Regardless of the interval between time points, the respiratory state predictor (230) reviews the input images and may compute a respiratory state signal y (232) for each of the medical images in the sequence. For example, the respiratory state signal $y_t$ will correspond to the medical image collected at time t. In some examples of the invention, all respiratory state signals in the sequence of medical images are compared to each other to ensure all respiratory states across the timepoints are within a threshold (explained further below and in EQ. 1.3) to each other, thus guarding against the influence that variations in a respiratory state can have over the assessment of progression of a lung condition from medical images. In other examples of the invention, it may suffice to compare the respiratory state signals of every two consecutive timepoints to ensure the respiratory state signals are within a threshold to each other. In some examples, the comparison between respiratory state signals is obtained in the following way:

$$\text{Maximum Respiration Difference(MRD)} = \max(\text{abs}(y_j - y_i)) \forall i,j \in T \quad (1.3)$$

Where T is the set of indices of the timepoints of the medical images in the input sequence. Therefore, (1.3) measures the maximum absolute difference of the respiratory state signal y between any pair of images in the sequence. The maximum respiration difference should fall below a threshold $TH_{mrd}$ otherwise a warning is issued stating that the assessment for multi-timepoint images may be unreliable due to variations in the respiratory states:

$$CADx \text{ Output} = \begin{cases} DiseaseRiskscore, & MRD \geq TH_{mrd} \\ DiseaseRiskscore \text{ and } RespiratoryStateWarning, & MRD > TH_{mrd} \end{cases} \quad (1.4)$$

When deploying a CADx device, such as shown in FIG. 2 or 3, it is critical to have mechanisms for detecting and preventing misuse of the device. One of such undesired scenarios is using the CADx device (120) to assess data that is not acquired at the optimal respiratory state. For example, in an embodiment of the invention, when assessing lung nodules for cancer risk, it is generally recommended that the image scan, preferably a CT scan, is acquired while the patient is in full inhalation. However, there are scenarios where the medical image scans are captured for a different purpose where the respiratory state requirements were different, or the patient was unable to stay in the optimum respiratory state. To assure the safe use of the CADx device even in those unexpected scenarios, this invention builds an automatic respiratory state assessor into a CADx device to further ensure that input data to the CADx device with unacceptable respiratory states are warned to the user.

This invention can be applied in any context where a CADx device, powered by a machine learning model, is used to assess the risk of lung disease, preferably lung cancer from the input medical images.

This invention can be applied in any context where a CADx device, powered by a machine learning model, is used to assess the risk of disease from input medical data such as medical images.

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system. Therefore, some examples describe a non-transitory computer program product having executable program code stored therein for receiving at least one input medical image of a patient in which the patient's lungs are visible.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media e.g., CD ROM, CD R, etc. and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing running program or portion of a program, current program values and state information, and the resources used by the operating system to manage the execution of the process. An operating system OS is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output I/O devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

We claim:

1. A Computer Aided Diagnosis, CADx system for reviewing medical images to determine if the images are acceptable for further analysis by the CADx system by determining a disease risk score, by identifying the respiratory state of the lungs as shown in a medical image, the system comprising:
    an input circuit for receiving at least one medical image;
    a respiratory state assessor circuit for determining the respiratory state of the lungs in the input medical image where the respiratory state assessor is trained using a machine learning model with a plurality of training images showing a range of different respiratory states, the training of the machine learning model comprising the steps of:
    providing a training dataset of input images with corresponding ground truth labels which indicate a respiratory state at which the image was acquired;
    providing at least one image from the training set to a respiratory state predictor to output a respiratory state prediction;
    comparing the respiratory state prediction with the corresponding ground truth label to determine to accuracy of the machine learning model;
    repeating the above steps until the variation between the prediction and the ground truth level reaches a pre-set level;
    and
    an output circuit to produce an output confirming the respiratory state of the input image.

2. A Computer Aided Diagnosis, CADx system according to claim 1, wherein the output is a warning about the respiratory state of the input image that the input image is not an acceptable state.

3. A Computer Aided Diagnosis, CADx system according to claim 2, wherein the warning is one or more of an audio or visual warning.

4. A Computer Aided Diagnosis, CADx system according to claim 2, wherein the CADx system will further analyse the input image when, after review of the input image, the input image has a warning about the acceptability of the input image.

5. A Computer Aided Diagnosis, CADx system according to claim 1, wherein when the output circuit confirms that the respiratory state of input image is an acceptable respiratory state, the image is passed for further analysis by the CADx system.

6. A Computer Aided Diagnosis, CADx system according to claim 5, wherein the output from the further analysis comprises a disease risk score for the input image.

7. A Computer Aided Diagnosis, CADx system according to claim 1, wherein the input image is one of: a CT image, an MRI image, a PET image, an X-ray image, an ultrasound image or a SPECT image.

8. A Computer Aided Diagnosis, CADx system according to claim 7, wherein the input image comprises an image showing at least part of a lung.

9. A Computer Aided Diagnosis, CADx system as claimed in claim 1, wherein the input further comprises one or more of: biomarkers for the patient or clinical parameters for the patient.

10. A Computer Aided Diagnosis, CADx system according to claim 9, wherein the clinical parameters and biomarkers comprise at least one of: patient age, patient sex, results of blood tests, results of lung function tests.

11. A Computer Aided Diagnosis, CADx system according to claim 1, wherein the respiratory state assessor circuit determines the respiratory state of the input image by generating a respiratory state signal and comparing the signal to a predefined threshold, where the input image is acceptable if the respiratory state signal exceeds the threshold.

12. A Computer Aided Diagnosis, CADx system according to claim 11, wherein the output of the CADx system is determined according to the following threshold relationship:

$$CADx \text{ Output} = \begin{cases} DiseaseRiskscore, & y \geq TH_{Resp} \\ DiseaseRiskscore \text{ and } RespiratoryStateWarning, & y < TH_{Resp} \end{cases}$$

where $TH_{resp}$ is the respiratory threshold.

13. A Computer Aided Diagnosis, CADx system as claimed in claim 12, wherein the threshold can determine if the input image shows full exhalation, partial inhalation, or full inhalation.

14. A Computer Aided Diagnosis, CADx system as claimed in claim 13, wherein the exhalation status is determined by:

$$PercentageInhalation = \begin{cases} \text{Full exhalation,} & y < TH_{lvl1} \\ \text{Partial inhalation,} & TH_{lvl1} \leq y < TH_{lvl2} \\ \text{Full inhalation,} & y \geq TH_{lvl2} \end{cases}$$

where $TH_{lvl1}$ and $TH_{lvl2}$ are inhalation thresholds.

15. A method for analysing medical thoracic images for determining if the images are acceptable for analysis, by identifying the respiratory state of the lungs as shown in a medical image, the method comprising the following:
    receiving at least one input medical image;
    determining the respiratory state of the lungs in the input medical image using a respiratory state assessor, where the respiratory state assessor is trained using a machine learning model with a plurality of training images showing a range of different respiratory states, the training of the machine learning model comprising the steps of:
    providing a training dataset of input images with corresponding ground truth labels which indicate a respiratory state at which the image was acquired;
    providing at least one image from the training set to a respiratory state predictor to output a respiratory state prediction;
    comparing the respiratory state prediction with the corresponding ground truth label to determine to accuracy of the machine learning model;
    repeating the above steps until the variation between the prediction and the ground truth level reaches a pre-set level; and
    producing an output confirming the respiratory state of the input image.

16. A method according to claim 15, further comprising the step of providing the input image to a CADx system for analysis of the input image when the input image has a warning about the acceptability of the input image.

* * * * *